United States Patent [19]

Isogawa et al.

[11] Patent Number: 5,467,150
[45] Date of Patent: Nov. 14, 1995

[54] APPARATUS FOR MEASURING A CORNEA SHAPE

[75] Inventors: Shuichi Isogawa, Fujisawa; Nobuyuki Miyake, Yokohama, both of Japan

[73] Assignee: Nikon Corporation, Tokyo, Japan

[21] Appl. No.: 246,765

[22] Filed: May 20, 1994

[30] Foreign Application Priority Data

May 26, 1993 [JP] Japan ................................. 5-123783

[51] Int. Cl.⁶ ............................................. A61B 3/10
[52] U.S. Cl. ........................................... 351/212; 351/211
[58] Field of Search ................................. 351/211, 205, 351/212, 221, 247; 356/376

[56] References Cited

U.S. PATENT DOCUMENTS

| | | | |
|---|---|---|---|
| 4,999,009 | 3/1991 | Matsumura | 351/212 |
| 5,080,477 | 1/1992 | Adachi | 351/212 |
| 5,243,367 | 9/1993 | Spellitz | 351/212 |

FOREIGN PATENT DOCUMENTS

| | | | |
|---|---|---|---|
| 1292727 | 2/1987 | U.S.S.R. | 351/247 |
| 86/02249 | 4/1986 | WIPO | 351/247 |

*Primary Examiner*—William L. Sikes
*Assistant Examiner*—Huy Mai

[57] ABSTRACT

An apparatus for measuring a cornea shape is capable of arbitrarily changing the diameter of ring illumination projected onto the cornea. The apparatus includes a light source for supplying a beam of light, a scanner system for scanning the beam of light from the light source and forming a light spot describing a circular locus on the surface of the cornea, and a device for observing therethrough the shape of the cornea on the basis of the locus described by the beam of light reflected by the cornea. The scanner system includes a reflecting mirror having a zonal reflecting surface disposed around the cornea, and a light deflector for directing the beam of light from the light source to the zonal reflecting surface.

8 Claims, 3 Drawing Sheets

APPARATUS FOR MEASURING A CORNEA SHAPE

BACKGROUND OF THE INVENTION

1. Field of the Invention

This invention relates to an apparatus for optically measuring the surface shape of the cornea of an eye to be examined.

2. Related Background Art

There is known an apparatus in which in order to measure the shape of a cornea, an index mark of a particular shape is projected onto the cornea, the reflected image from the surface of the cornea is passed through a measuring optical system to form a projected image including the shape of the cornea as information on the light receiving surface of a light receiving element and data obtained on the basis of the photoelectric output of the light receiving element is calculation-processed to thereby determine the surface shape of the cornea.

For example, U.S. Pat. No. 4,999,009 discloses an apparatus in which the index mark of a ring-shaped slit is projected onto the cornea of an eye to be examined. There is also known an apparatus in which concentric circular patterns are projected onto the cornea of an eye to be examined through a plurality of concentric circular slits and the surface shape of the cornea is measured on the basis of the analysis of the shapes of the reflected images thereof from the cornea.

However, for highly accurate measurement, it is necessary that more ring slit patterns differing in diameter can be projected onto the surface of the cornea, and the prior-art construction using concentric circular slits has had a limitation and has suffered from the problem that the apparatus becomes bulky.

SUMMARY OF THE INVENTION

It is an object of the present invention to provide an apparatus for measuring a cornea shape in which the diameter of ring illumination projected onto the cornea of an eye to be examined can be arbitrarily changed.

It is another object of the present invention to provide an apparatus for measuring a cornea shape in which ring illumination of any diameter is projected onto the surface of the cornea, whereby the surface shape of the cornea at a designated position can be measured.

It is still another object of the present invention to provide an apparatus in which the diameter of ring illumination is continuously varied, whereby shape measurement at any position on the surface of a cornea and close measurement of the shape of the whole surface of the cornea are possible.

An apparatus for measuring a cornea shape according to the present invention includes a light source for supplying a beam of light, a scanner system for scanning the beam of light from said light source and forming a light spot describing a circular locus on the surface of a cornea, and means for observing therethrough the shape of the cornea on the basis of the locus described by said beam of light reflected by the cornea.

In a preferred embodiment of the present invention, the scanner system includes a reflecting mirror having a zonal reflecting surface disposed around the cornea, and a light deflector for directing the beam of light from the light source to the zonal reflecting surface.

DETAILED DESCRIPTION OF THE PREFERRED EMBODIMENTS

An embodiment of an apparatus for measuring a cornea shape according to the present invention will hereinafter be described with reference to the drawings.

Figure 1:
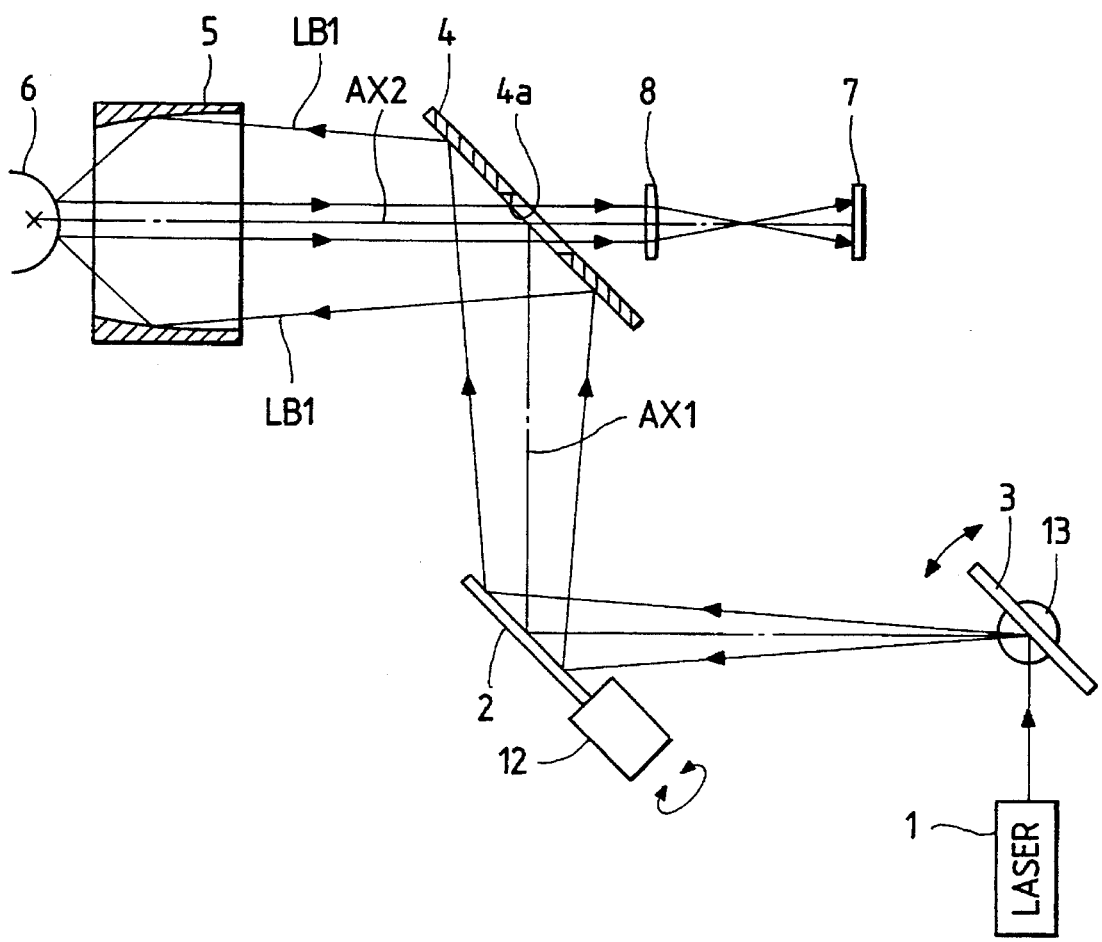
FIG. 1 is a schematic view showing the optical arrangement of an apparatus according to an embodiment of the present invention.

In FIG. 1, a light source 1, a pair of scanning mirrors 2 and 3 constituting a light deflector, an apertured mirror 4 and an internal reflecting mirror 5 together constitute an optical system for forming a light spot describing a circular locus on the surface of the cornea of an eye 6 to be examined.

The light source 1 emits collimated visible light, and may preferably be a laser. The scanning mirror 2 is mounted on an X-direction actuator 12 and swings about an axis perpendicular to the plane of the drawing sheet of FIG. 1. Each actuator 12, 13 is constituted, for example, by a galvanometer, and responds to a pair of sine waves outputted from a controller to be described which are 90° out of phase with each other.

Figure 2:
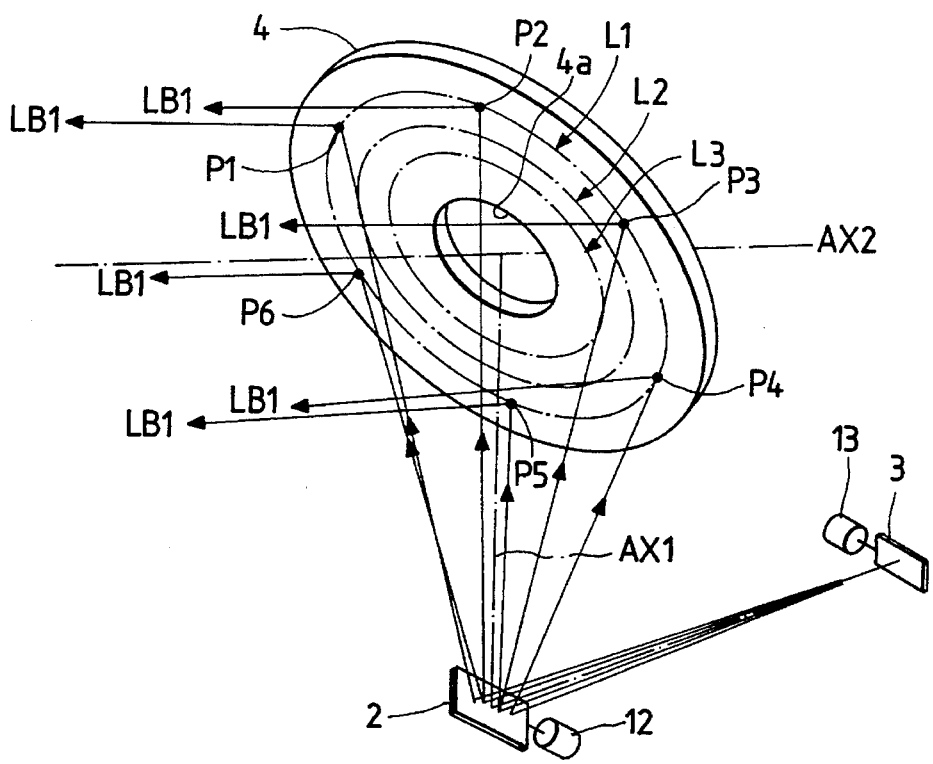
FIG. 2 is a perspective view showing the locus of a light spot described on the reflecting surface of an apertured mirror by a pair of scanning mirrors.

The apertured mirror 4 is an elliptical mirror having an opening 4a at the center thereof, and is inclined with respect to the eye to be examined. A beam of light reflected by the scanning mirrors 2 and 3 impinges on a reflecting surface around the opening 4a and is reflected toward he reflecting mirror 5. Since a pair of sine waves which are 90° out of phase with each other are inputted to the actuators 12 and 13, the beam of light reflected by the scanning mirrors 2 and 3 describes a circular locus on a plane perpendicular to an optical axis AX1 and as a result, on the reflecting surface of the apertured mirror 4, the above-described beam of light forms a light spot describing an elliptical locus L1 linking points P1–P6 together, as shown in FIG. 2. As will be described later, if the amplitudes of the pair of sine waves are controlled, the amplitude of the swinging movement of the scanning mirrors 2 and 3 will vary and the size of the ellipse described on the mirror 4 could be continuously varied with the range of L1–L3.

Figure 3:
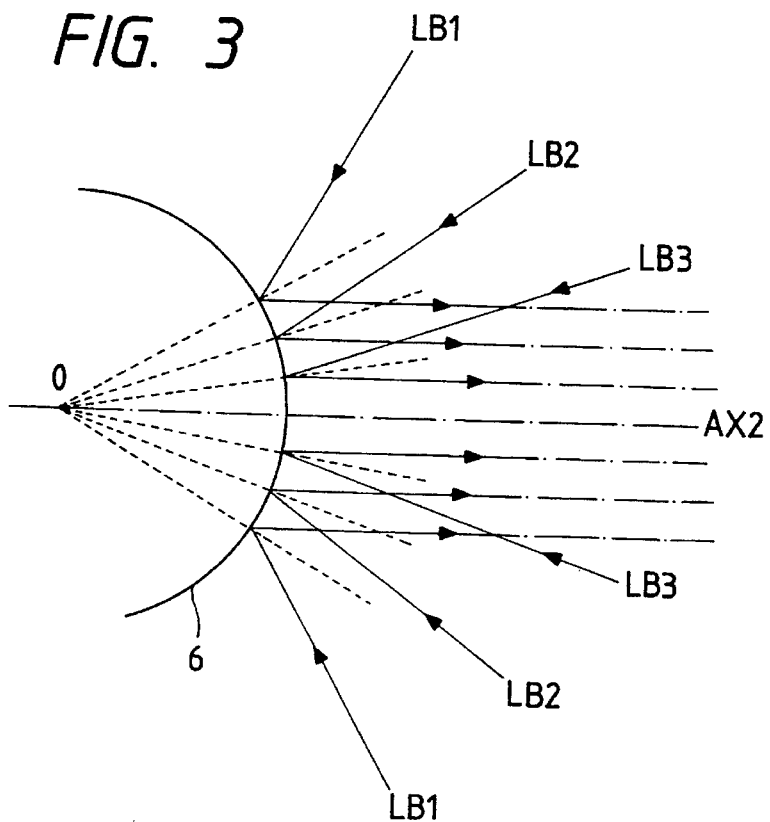
FIG. 3 is an optical path view illustrating the states of beams of light applied to the surface of a cornea.

The reflecting mirror 5 is a cylindrical mirror having an internal reflecting surface constituted by an aspherical surface of which the meriodional cross-section is a curve approximate to a parabola, and reflects the beam of light reflected by the apertured mirror 4 toward the surface of the cornea of the eye to be examined. The states of beams of light incident on the cornea are shown in FIG. 3. A beam of light LB1 is the reflected beam of light from the mirror 4 at the position of the locus L1, a beam of light LB2 is the reflected beam of light at the position of the locus L2, and a beam of light LB3 is the reflected beam of light at the position of the locus L3. That is, the reflected beam of light from the mirror 4 varies within the range of LB1–LB3 in accordance with a variation in the angles of swinging of the scanning mirrors 2 and 3. The shape of the internal reflecting surface of the reflecting mirror 5 is designed such that the beams of light LB1, LB2 and LB3 describe rings differing in diameter on the surface of the cornea, and is also designed such that when the cornea of the eye to be examined is an ideal spherical surface, these beams of light LB1, LB2 and LB3 are reflected by the cornea and are reflected in directions substantially parallel to an optical axis AX2.

An observation optical system comprised of a condensing lens 8 and a light receiving element 7 is disposed behind the apertured mirror 4. The condensing lens 8 condenses the reflected beam of light from the cornea passed through the opening 4a in the mirror 4 on the light receiving element 7. The light receiving element 7 is comprised, for example, of a two-dimensional changed-coupled device CCD, and a pattern formed on the light receiving surface thereof includes information based on the surface shape of the cornea of the eye to be examined.

Figure 4:
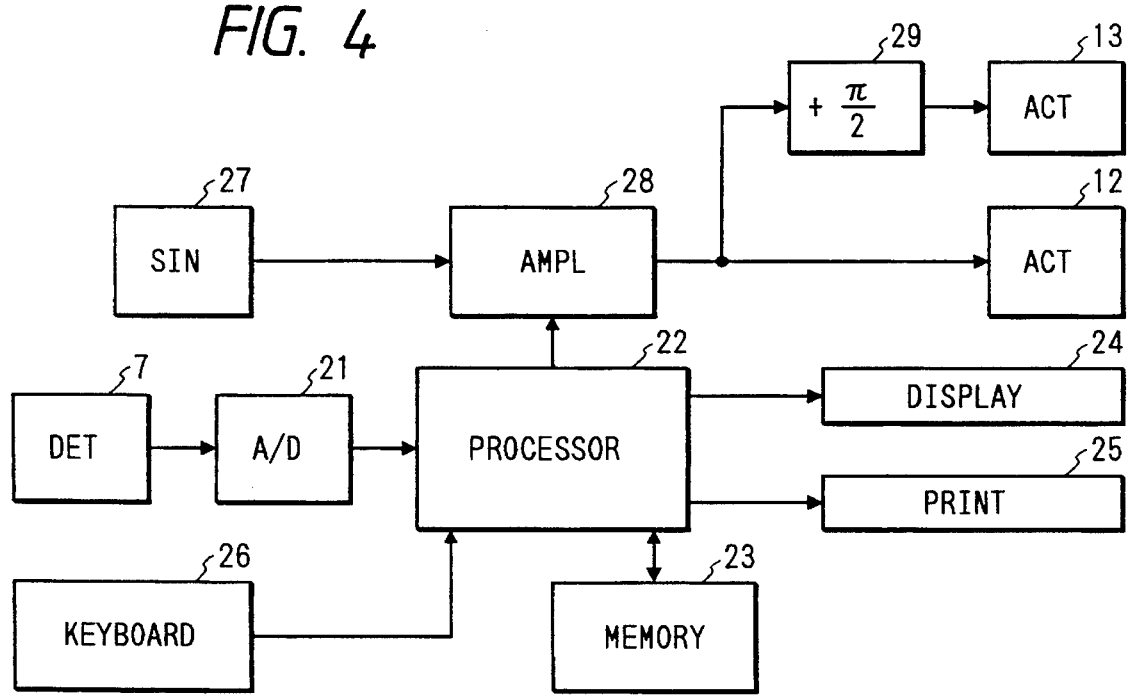
FIG. 4 is a block circuit diagram showing the construction of a controller according to the present invention.

The photoelectric output of the light receiving element 7 is digitalized by the A/D converter 21 of a controller shown in FIG. 4, and is recorded as measurement data in a frame memory 23 through a calculation processing circuit 22. The calculation processing circuit 22 reads out the measurement data recorded in the frame memory 23 and displays on a display 24 the pattern formed on the light receiving surface of the light receiving element 7. Further, the calculation processing circuit 22 executes calculation processing for obtaining the measured value of the surface shape of the cornea on the basis of the measurement data in accordance with the operation of a keyboard 26, causes the display 24 to display the result, and outputs the measured value to a printer 25.

The controller is further provided with a sine wave generating circuit 27, a variable amplifier 28 and a 90° phase shifter 29. The calculation processing circuit 22 changes the amplification factor of the variable amplifier 28 in accordance with the operation of the keyboard 26 and varies the amplitude of a sine wave signal outputted from the sine wave generating circuit 27. The sine wave signal amplified by the amplifier 28 is directly inputted to the actuator 12 and also is phase-shifted by 90° by the phase shifter 29, whereafter it is inputted to the actuator 13.

When the keyboard 26 is operated by a measurer and the controller is instructed to start measurement, the calculation processing circuit 22 determines the amplification factor of the amplifier 28 in accordance with an operation program, and drives the actuators 12 and 13. The beam of light from the light source 1 arrives at the surface of the cornea of the eye 6 to be examined via the scanning mirrors 2, 3, the apertured mirror 4 and the reflecting mirror 5, and forms on the surface a light spot describing a ring-shaped locus having a predetermined diameter. The reflected beam of light from the cornea is condensed by the condensing lens 8, and describes on the light receiving surface of the light receiving element 7 a ring-shaped locus having a distortion conforming to the surface shape of the cornea. For example, when the cornea has astigmatism, the beam of light projected onto the light receiving surface describes an elliptical locus. The calculation processing circuit 22 processes the output of the light receiving element 7 and causes the display 24 to display the locus of the ring on the light receiving surface.

When the measuring position on the cornea is to be changed, if the change of the diameter of the ring is inputted to the keyboard 26, the amplification of the amplifier 28 will be changed by the calculation processing circuit 22 and the amplitude of the sine wave signal will be enlarged or reduced. Accordingly, it is possible to measure the surface shape of the cornea at any radial position as required while observing the ring shape displayed.

If an operation program for continuously changing the amplification factor of the amplifier 28 is prepared in advance, it will be possible to continuously describe a plurality of rings differing in diameter on the surface of the cornea. Thereby, there will be obtained the same effect as that when a number of ring light sources are projected and therefore, the measurement of the whole surface of the cornea of the eye to be examined will become possible.

What is claimed is:

1. An apparatus for measuring a cornea shape comprising:

a light source for supplying a beam of light;

a scanner system for scanning the beam of light from said light source and forming a light spot describing a circular locus on the surface of said cornea, said scanner system including a reflecting mirror having a zonal reflecting surface disposed around said cornea, and a light deflector for directing the beam of light from said light source to said zonal reflecting surface; and means for observing therethrough the shape of said cornea on the basis of the locus described by said beam of light reflected by said cornea.

2. The apparatus of claim 1, wherein said light deflector includes a pair of scanning mirrors disposed in series in the direction of travel of the beam of light from said light source, and a pair of actuators for swinging said pair of scanning mirrors about axes orthogonal to each other.

3. The apparatus of claim 2, wherein said light deflector further includes a controller for outputting a pair of sine wave signals which are 90° out of phase with each other, and said pair of actuators are responsive to said pair of sine wave signals to swing said pair of scanning mirrors.

4. The apparatus of claim 3, wherein said controller includes a variable amplifier for amplifying said pair of sine wave signals, and said pair of actuators vary the angles of swinging of said pair of scanning mirrors in accordance with the amplitudes of said pair of sine wave signals.

5. The apparatus of claim 4, wherein said controller includes an operating device input-operated to change the diameter of the circular locus described on the surface of said cornea, and a calculation processing circuit for determining the amplification factor of said variable amplifier on the basis of the input of said operating device.

6. An apparatus for measuring a cornea shape comprising:

a light source for supplying a beam of light;

a scanner system for scanning the beam of light from said light source and forming a light spot describing a circular locus on a surface of said cornea;

said scanner system including a pair of scanning mirrors disposed in series in the direction of travel of the beam of light from said light source, a controller outputting a pair of sine wave signals which are 90 degrees out of phase with each other, and a pair of actuators for swinging said pair of scanning mirrors about axes orthogonal to each other; and means for observing therethrough the shape of said cornea on the basis of the locus described by said beam of light reflected by said cornea.

7. The apparatus of claim 6, wherein said controller includes a variable amplifier for amplifying said pair of sine wave signals, and said pair of actuators varies the angles of swinging of said pair of scanning mirrors in accordance with the amplitudes of said pair of sine wave signals.

8. The apparatus of claim 7, wherein said controller includes an operating device input-operated to change the diameter of the circular locus described on the surface of said cornea, and a circulation processing circuit for determining the amplification factor of said variable amplifier or the basis of the input of said operating device.

* * * * *